(12) United States Patent
Pickhard

(10) Patent No.: US 6,743,203 B1
(45) Date of Patent: Jun. 1, 2004

(54) DEVICE FOR AUTOMATICALLY INJECTING INJECTION LIQUIDS

(75) Inventor: Ewald Pickhard, Grossebersdorf (AT)

(73) Assignee: Pharma Consult Ges.m.b.H., Vienna (AT)

( * ) Notice: Subject to any disclaimer, the term of this patent is extended or adjusted under 35 U.S.C. 154(b) by 165 days.

(21) Appl. No.: 10/031,924

(22) PCT Filed: Jul. 27, 2000

(86) PCT No.: PCT/AT00/00207

§ 371 (c)(1),
(2), (4) Date: May 3, 2002

(87) PCT Pub. No.: WO01/07104

PCT Pub. Date: Feb. 1, 2001

(30) Foreign Application Priority Data

Jul. 27, 1999 (AT) .............................. 509/99 U

(51) Int. Cl.$^7$ .............................. A61M 5/00; A61M 5/20
(52) U.S. Cl. ..................... 604/139; 604/110; 604/157
(58) Field of Search ................... 604/110, 187, 604/197, 198, 200, 201, 218, 220, 232, 240, 243, 244, 131, 134–136, 139, 156, 157

(56) References Cited

U.S. PATENT DOCUMENTS 5,658,259 A   8/1997   Pearson et al.
5,695,472 A   12/1997  Wyrick
5,709,668 A   1/1998   Wacks

FOREIGN PATENT DOCUMENTS

| AT | 303251 | 11/1972 | ............ A61M/5/20 |
| DE | 4037418 A1 | 5/1991 | ............ A61M/5/20 |
| DE | 19532410 A1 | 3/1997 | ............ A61M/5/31 |
| EP | 0154593 | 9/1985 | ............ A61M/5/20 |
| EP | 0 409 365 A1 | 1/1991 | ............ A61M/5/20 |
| EP | 0695554 A2 | 2/1996 | ............ A61M/5/20 |
| GB | 933976 | 8/1963 | |

*Primary Examiner*—Michael J. Hayes
(74) *Attorney, Agent, or Firm*—Chapman and Cutler LLP

(57) ABSTRACT

The invention concerns a device for automatically injecting injection liquids, comprising an axially divided housing, whereof the parts can be removably assembled. In a first part of the housing (13) is guided an axially mobile pressure pin (14) which can be driven in against a force accumulator (15), which can be locked once it has been driven in and can come out when the force accumulator (15) is released. In a second part of the housing (1) are arranged, axially mobile, an injection needle (4) maintained in a needle guide (5) and an ampoule (3). Said injection needle (4) maintained in the needle guide (5) can be axially mobile, relative to the ampoule (3), and has, on its side facing the ampoule (3), a perforation part (23) designed to perforate the ampoule (3). The second part of the housing (1) can be closed with a top (11) at its open end facing the first part of the housing (13).

4 Claims, 3 Drawing Sheets

DEVICE FOR AUTOMATICALLY INJECTING INJECTION LIQUIDS

Figure 1:
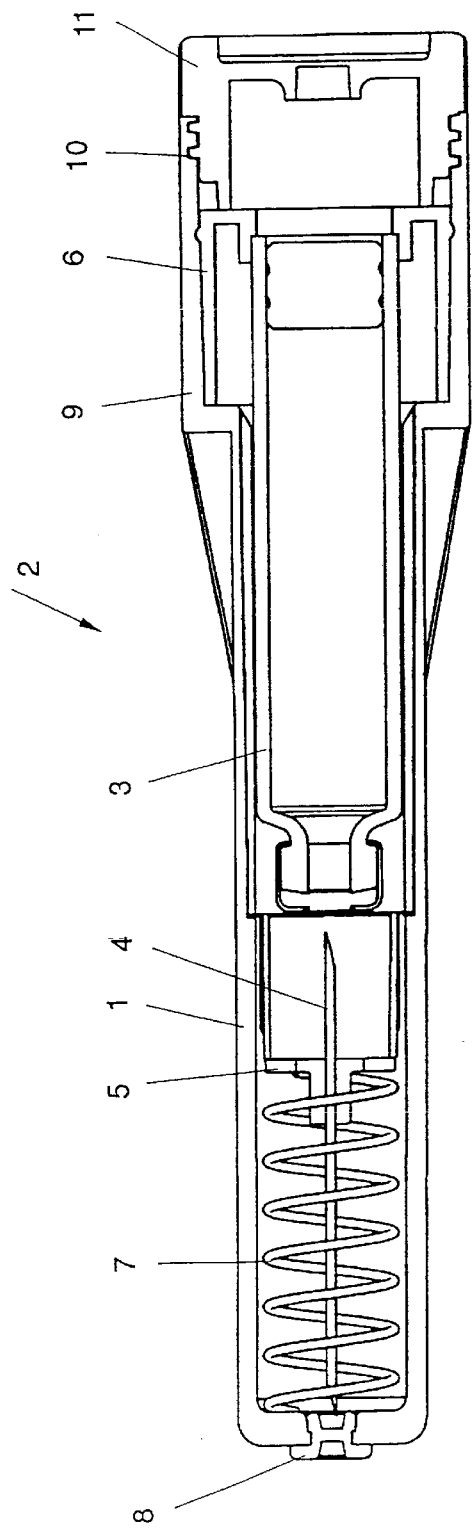

The invention relates to a device for automatically injecting injection liquids, including an axially subdivided housing whose parts are detachably connectable, wherein an axially displaceable pressure pin is guided in a first housing part, which pin is capable of being inserted against a force accumulator and locked in the inserted position and extended upon relief of said force accumulator, and wherein an injection needle fitted within a needle guide and an ampoule are mounted in a second housing part in an axially displaceable manner.

Devices of the initially mentioned kind have become known as autoinjectors. The known devices are pen-sized instruments which facilitate the injection of an emergency agent into the body in the event of an emergency situation. Autoinjectors are employed, for instance, in allergic emergency situations, e.g., in the event of insect or snake bites etc., but also in the military field, for instance, in order to rapidly counteract intoxications by C warfare agents. The known devices are usually designed as disposable devices, thus being disposed of after a one-time use.

From AT 303 251, an injection device is known, which comprises two housing parts capable of being screwed one into the other, the activator containing a spring-loadable pressure pin and the injector containing the ampoule as well as the injection needle as an inseparable unit. After having unlocked the spring-loaded pressure pin, the latter exerts a force on the piston plug of the ampoule, whereupon, at first, the ampoule is displaced in the axial direction together with the injection needle within the injector housing so as to cause the injection needle to penetrate into the body surface, and the liquid contained in the ampoule is subsequently set under such a high pressure that a sealing membrane provided between the ampoule and the injection needle will break, thus causing the liquid to be ejected. That known configuration, however, has the drawback that the broken membrane may obstruct the injection needle, thus preventing the rapid ejection of the injection liquid. Furthermore, that configuration constitutes a problem connected with the disposal of the autoinjector after use, since the injection needle projects out of the housing and, thus, constitutes a high risk of injury and infection.

The previously known autoinjectors, furthermore, have the drawback of rendering the safe storage and transportation of stand-by ampoules unfeasible. The ampoule can be inserted into the autoinjector only at works. Moreover, with the known autoinjectors, another whole autoinjector must always be taken along as a stand-by autoinjector.

The invention aims to provide a device of the initially defined kind, which can be disposed of without any risk of injury or infection and the disposal of which, in addition, is feasible in as environmentally safe a manner as possible by minimizing the number of parts to be disposed of. At the same time, the invention aims to provide a storing and transporting container for the ampoules, in which the filled glass ampoule can be stored over years in a safely protected and tightly sealed manner. In particular, it is to be feasible to carry along several ampoules containing different injection liquids and/or stand-by ampoules while minimizing the parts to be carried along. To solve this object, the device according to the invention essentially consists in that the injection needle fitted in the needle guide is mounted so as to be displaceable in the axial direction relative to the ampoule and, on its side facing the ampoule, is designed as a perforation piece for the ampoule, and that the second housing part, on its open end facing the first housing part, is closable by a sealing cap. By designing the injection needle as a perforation piece for the ampoule on its side facing the ampoule and mounting the injection needle so as to be displaceable in the axial direction relative to the ampoule, it is feasible to mount the ampoule in the interior of the second housing part, i.e., the injector, without being firmly connected with the injection needle. The injection liquid may, thus, be safely stored in the ampoule over years without the ampoule being firmly connected with any of the other structural components and the stability of the injection liquid being negatively affected. The use of an ampoule, moreover, substantially facilitates the manufacture of the injector part and, in addition, offers the advantage that a larger selection of different injection liquids will be available than with ready-made syringes.

It is only in use that the ampoule is displaced in the direction of the injection needle under the force of the pressure pin extended upon relief of the force accumulator, and pierced by the injection needle designed as a perforation piece on its side facing the ampoule. Thereby, any obstruction of the injection needle will be reliably prevented and it will be ensured that the injection liquid may leave the ampoule unhampered, after the injection needle has been pushed out of the injector housing and penetrated the tissue.

By making the second housing part closable by a sealing cap on its open end facing the first housing part, a storing and transporting container for the glass ampoule as well as a disposal container for the used injection needle and the empty ampoule is simultaneously provided. The housing part enclosing the ampoule and the needle may, thus be stored and transported separately from the activator part, the ampoule and the needle being protected in a breakage-proof manner and sealed in a bacteria-tight manner over years by means of the sealing cap. Thus, the carrying along of several different ampoules is, above all, facilitated. The activator part which can be carried along separately may be connected with the injector part containing the respective injection liquid according to demands. The carrying along of several activator parts is not necessary, since the activator is reusable.

The housing part enclosing the needle will be even more suitable for use as a disposal container, if the ampoule and/or the needle guide are advantageously mounted in a resilient manner. After the use of the autoinjector, the injector part is detached from the activator with the used injection needle projecting out of the injector housing automatically getting back into the interior of the housing due to the action of a resilient component. In this context, the configuration may be devised such that a helical spring is arranged in the interior of the second housing part between the housing end including the passage opening for the injection needle and the needle guide. Due to the fact that the second housing part, on its end including the passage opening for the injection needle, is advantageously closed by an elastic sealing disc, the needle-side end of the injector housing will always remain tight such that no sealing cap need be slipped on.

If the use of a resilient component acting on the needle guide or the ampoule is obviated, the injection needle may be pushed back into the housing after the use of the autoinjector by putting or screwing a sealing cap on that end of the second housing part out of which the used injection needle projects. The injector will be closed in any event on its open end facing the first housing part, i.e., the activator, thus forming a disposal container safely and sealingly receiving the used injection needle and the empty ampoule.

Any injury or infection by the disposed parts is thereby excluded, and the number of parts to be thrown away is further minimized. As a result, the activator may be reused by inserting the pressure pin against a force accumulator and locking it in the inserted position and connecting the activator with a new injector. A new, unused injector will always be closed by a sealing cap prior to its first use, thus providing a storing and transporting container for the glass ampoule, by which the sterility of the ampoule and the needle unit will be safeguarded. Consequently, several injectors containing different injection liquids may, for instance, be carried along with the appropriate injector being connectable to the activator upon detachment of the sealing cap in an emergency case.

As already mentioned, the device according to the invention is devised such that the injection needle carrying the perforation piece for the ampoule is mounted so as to be axially displaceable relative to the ampoule by a needle guide. It is thereby ensured that the injection needle mounted so as to be axially displaceable by a needle guide, upon the action of force by the pressure pin on the piston of the ampoule, will, at first, be displaced in the axial direction and penetrate the tissue through the skin on the desired site, and the perforation piece of the injection needle will break the ampoule only after this, wherein the needle guide, on its jacket, advantageously comprises at least one inwardly salient resilient abutment piece for the ampoule and, furthermore, at least one outwardly salient resilient abutment piece which cooperates with an appropriate stop of the second housing part. The inwardly salient resilient abutment piece is dimensioned so as to offer a higher resistance against the force exerted by the pressure pin than the outwardly salient resilient abutment piece. As a result, the injection needle will, at first, penetrate the interior of the body while overcoming the force of the outwardly salient resilient abutment piece bending back in the direction towards the ampoule, whereupon the inwardly salient resilient abutment piece is being pushed inwardly into the needle guide as the perforation piece passes into the ampoule. Due to the outwardly salient resilient abutment piece cooperating with an appropriate stop of the second housing part in the transport and storage position, the needle guide can be precisely positioned and received within the housing in a manner secured in its position.

Advantageously, the device according to the invention is designed such that the sealing cap carries a thread or a bayonet capable of being screwed or latched with a counter-thread or counter-bayonet, respectively, provided on the open end of the second housing part.

In order to reliably prevent the ampoule from falling out of the second housing part after having been separated from the activator part, the configuration advantageously is devised such that a piece comprising a stop for the ampoule is lockable in a second housing part region that is designed to have an enlarged diameter, thus securing the ampoule against falling out. On account of the force of the expanding pressure spring acting on the needle guide, it is, thereby, safeguarded that neither the contaminated injection needle nor the then empty ampoule will fall out or be flung out of the second housing part.

Furthermore, the device according to the invention in a particularly advantageous manner is designed such that the counter-thread provided on the open end of the second housing part is capable of being screwed with a thread of the first housing part. This enables the counter-thread provided on the second housing part to be screwed with the sealing cap, on the one hand, and, upon detachment of the sealing cap, with the activator, on the other hand.

Figure 2:
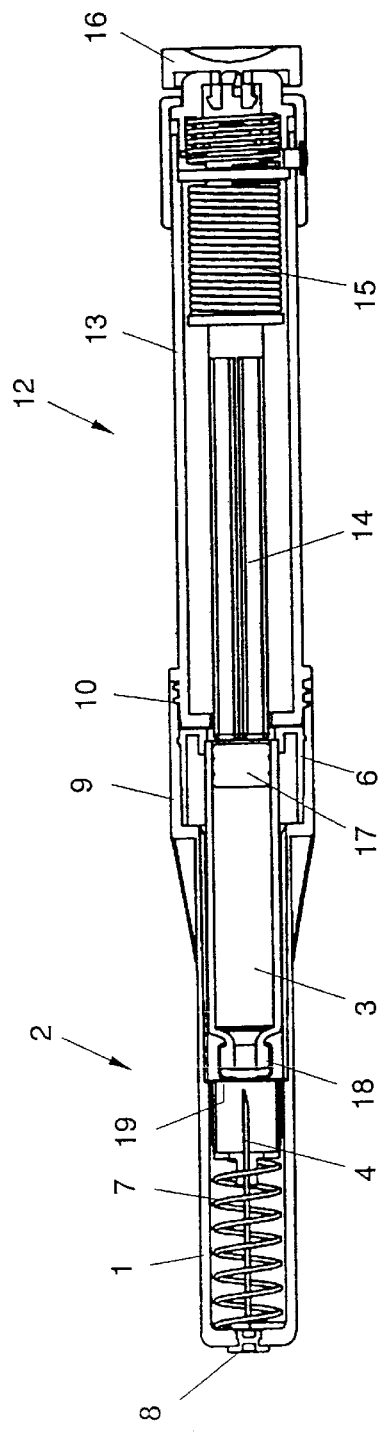
Figure 3:
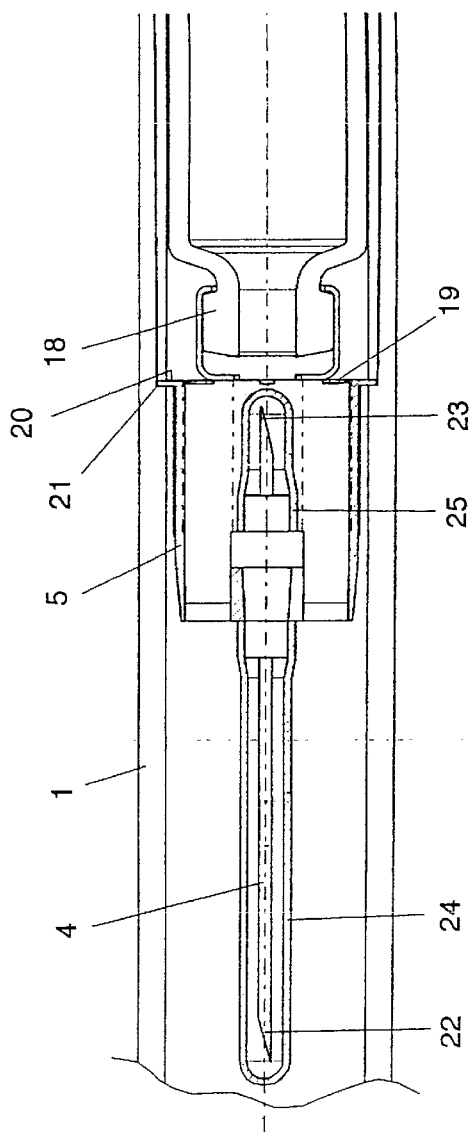
Figure 4:
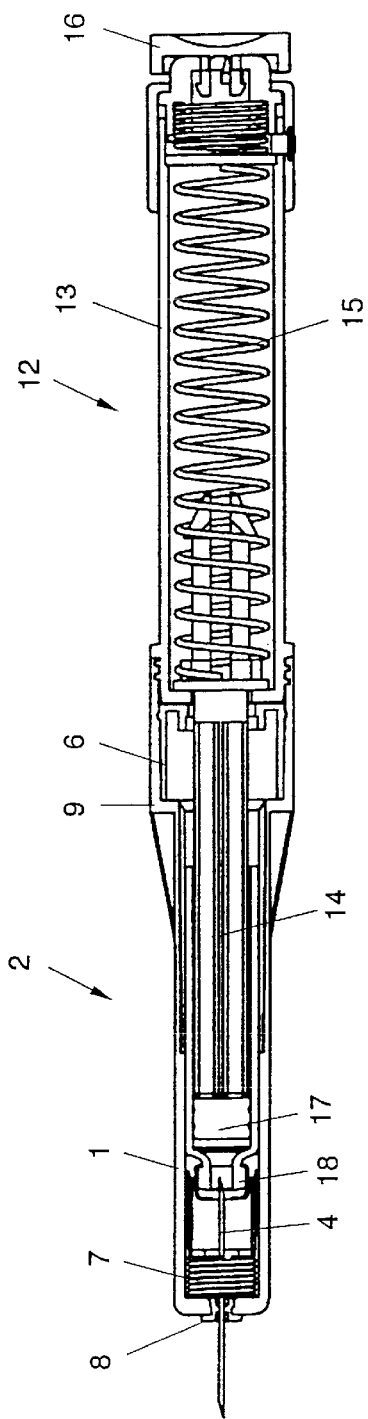
Figure 5:
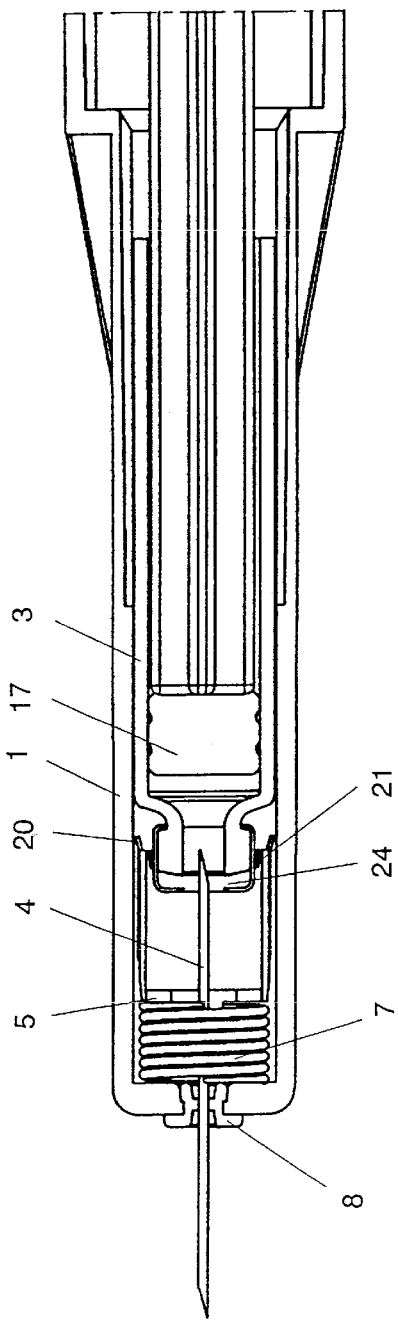
Figure 6:
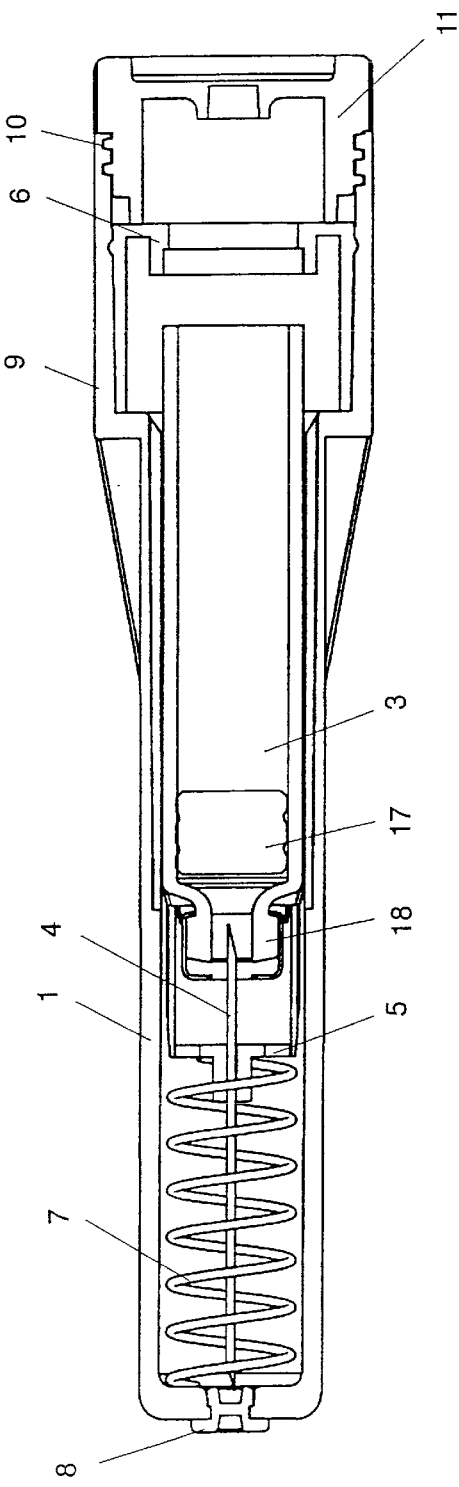

In the following, the invention will be explained in more detail by way of an exemplary embodiment schematically illustrated in the drawing. Therein, FIG. 1 illustrates the injector part of the device according to the invention with the sealing cap screwed on; FIG. 2 illustrates the injector part of the device according to the invention with the activator part screwed on, prior to the ejection of the injection liquid; FIG. 3 is a detailed view of FIG. 2; FIG. 4 shows a device of the invention according to FIG. 2 after the ejection of the injection liquid; FIG. 5 is a detailed view of FIG. 4; and FIG. 6 depicts the injector part of the device according to the invention with the sealing cap screwed on so as to be used as a disposal container.

FIG. 1 depicts the housing 1 of the injector part 2 of the device according to the invention. In the housing 1 are mounted in an axially displaceable manner an ampoule 3 and a needle guide 5 carrying the injection needle 4, a part 6 comprising a stop for the ampoule 3 being provided to secure said ampoule 3 against falling out. Furthermore, a helical spring 7 is arranged within the housing 1, whose function will be described farther below. The housing 1 is closed on its needle-side end by an elastic sealing disc 8. In the region 9, the housing 1 has a larger diameter as well as a thread 10 to enable a sealing cap 11 to be screwed thereon so as to provide a storing and transporting container for the filled glass ampoule 3.

In FIG. 2, the injector part 2 is screwed with the activator part 12. The activator part 12 is comprised of a housing 13 in which a pressure pin 14 is movably guided in an axially displaceable manner against the force of a spring 15. In the illustration according to FIG. 2, the pressure spring 15 is bent and the pressure pin 14 is locked in the extended position of the pressure pin. An actuation member 16 is provided on the rear end of the activator part 12 as a releasing means. The pressure pin 14 abuts on the ampoule piston 17, the ampoule 3, in turn, abuts on the resilient abutment piece 19 of the needle guide 5 in the region of the stepped collar 18. As is apparent, in particular, from FIG. 3, the needle guide 5 is formed with an outwardly salient abutment piece 20, which cooperates with a stop 21 of the housing 1 so as to ensure that the needle guide 5 is precisely positioned in the interior of the housing 1 and safely received in its position. From FIG. 3, it is, furthermore, apparent that the hollow needle 4 is designed as an injection needle 22 on its front end and as a perforation piece 23 on its ampoule-side end. In the illustration according to FIG. 3, the injection needle 4 is hermetically sealed by means of needle protection caps 24 and 25. Such needle protection caps may be used facultatively, in which case the elastic sealing disc 8 may be obviated.

After the actuation member 16 has been unlocked and axially lifted, the working stroke of the pressure pin 14 is released. The pressure pin 14 is moving forward in the axial direction as the spring 15 is being relieved and, with the interposition of the ampoule piston 17 which is not yet movable in the axial direction within the closed ampoule 3 and, furthermore, with the interposition of the resilient abutment piece 19, causes an axial displacement of the needle guide 5 such that the needle 4 emerges from the housing 1, while, at the same time, the outwardly salient resilient abutment piece 20 is being bent back in the direction towards the ampoule 3. In doing so, the elastic sealing disc 8 is perforated by the injection needle 22, whereby the spring 7 is compressed between the housing 1 and the needle guide 5. After the injection needle 4 has emerged from the housing 1, no further axial displacement of the needle guide 5 is feasible any more such that the force exerted on the ampoule piston 17 by the pressure pin 14 causes the resilient abutment piece 19 to become bent and then enables the ampoule 3 to move relative to the needle guide 5. In doing so, the ampoule side-end of the injection needle 4, which is designed as a perforation piece, pierces the ampoule seal 24 of the ampoule 3, thus enabling the injection liquid to be pressed out by the axial displacement of the ampoule piston 17 caused by the pressure pin 14.

FIG. 4 once again illustrates the device of the invention according to FIG. 2 with the ampoule 3 now being completely emptied, whereby it is apparent, in particular, from FIG. 5 how the abutments pieces 19 and 20, which offer differently high resistance forces to the force of the pressure pin 14, have become bent. The spring 7 is compressed in the instant case.

FIG. 6 depicts the injector part 2 screwed off the activator part 12 after use, with the injection needle 4 having been pushed back into the housing 1 by the pressure spring 7 acting on the needle guide 5. The housing 1 is again tightly closed on its needle-side end by the elastic sealing disc 8 such that the contaminated injection needle is located within the injector part 2 in a protected manner. The spring 7 additionally prevents the needle from moving so as to avoid a new perforation of the elastic sealing disc 8. The ampoule stop attached to part 6 and arranged within the housing prevents the ampoule 3 from falling out or being taken out. At the same time, the closing cap 11 is screwed in the thread 10 so as to enable also the other end to be tightly closed. In the main, this guarantees the optimum disposal and material separation while eliminating any risk of injury by the used injection needle at the same time.

What is claimed is:

1. A device for automatically injecting injection liquids, including an axially subdivided housing whose parts are detachably connectable, wherein an axially displaceable pressure pin is guided in a first housing part, which pin is capable of being inserted against a force accumulator and locked in the inserted position and extended upon relief of said force accumulator, and wherein an injection needle fitted within a needle guide and an ampoule are mounted in a second housing part in an axially displaceable manner, wherein the injection needle (4) is mounted so as to be displaceable in the axial direction relative to the ampoule (3) and, on its side facing the ampoule (3), is designed as a perforation piece (23) for the ampoule (3), characterized in that a helical spring (7) is arranged in the interior of the second housing part (1) between the housing end, including the passage opening for the injection needle (4) and the needle guide (5), that the needle guide (5), on its jacket, comprises at least one inwardly salient, axially resilient abutment piece (19) for the ampoule (3) and the needle guide (5), on its jacket, comprises at least one outwardly salient resilient abutment piece (20) which cooperates with an appropriate stop (21) of the second housing part, and that the second housing part (1), on its open end facing the first housing part (13), carries a thread or a bayonet capable of being screwed or latched with a counter-thread (10) or counter-bayonet, respectively, of the first housing part (13), or a sealing cap (11).

2. A device according to claim 1, characterized in that the second housing part (1), on its end, including the passage opening for the injection needle (4), is closed by an elastic sealing disc (8).

3. A device according to claim 1, characterized in that a piece (6) comprising a stop for the ampoule (3) is lockable in a second housing part region (9) that is designed to have an enlarged diameter, thus securing the ampoule (3) against falling out.

4. A device for automatically injecting injection liquids, including an axially subdivided housing whose parts are detachably connectable, wherein an axially displaceable pressure pin is guided in a first housing part, which pin is capable of being inserted against a force accumulator and locked in the inserted position and extended upon relief of said force accumulator, and wherein an injection needle fitted within a needle guide and an ampoule are mounted in a second housing part in an axially displaceable manner, wherein the injection needle (4) is mounted so as to be displaceable in the axial direction relative to the ampoule (3) and, on its side facing the ampoule (3), is designed as a perforation piece (23) for the ampoule (3), characterized in that a helical spring (7) is arranged in the interior of the second housing part (1) between the housing end, including the passage opening for the injection needle (4) and the needle guide (5), that the needle guide (5), on its jacket, comprises at least one inwardly salient, axially resilient abutment piece (19) for the ampoule (3) and the needle guide (5), on its jacket, comprises at least one outwardly salient resilient abutment piece (20) which cooperates with an appropriate stop (21) of the second housing part, and that the second housing part (1), on its open end facing the first housing part (13), carries a thread or a bayonet capable of being screwed or latched with a counter-thread (10) or counter-bayonet, respectively, of the first housing part (13), or a sealing cap (11), characterized in that the second housing part (1), on its end, including the passage opening for the injection needle (4), is closed by an elastic sealing disc (8), and characterized in that a piece (6) comprising a stop for the ampoule (3) is lockable in a second housing part region (9) that is designed to have an enlarged diameter, thus securing the ampoule (3) against falling out.

* * * * *